United States Patent [19]
Aoyagi

[11] Patent Number: 5,190,040
[45] Date of Patent: Mar. 2, 1993

[54] APPARATUS FOR MEASURING THE CHANGE IN THE CONCENTRATION OF A PIGMENT IN BLOOD

[75] Inventor: Takuo Aoyagi, Tokyo, Japan

[73] Assignee: Nihon Kohden Corporation, Tokyo, Japan

[21] Appl. No.: 743,618

[22] Filed: Aug. 12, 1991

Related U.S. Application Data

[63] Continuation-in-part of Ser. No. 515,527, Apr. 26, 1990, abandoned, which is a continuation of Ser. No. 138,111, Dec. 28, 1987, abandoned.

[30] Foreign Application Priority Data

Dec. 26, 1986 [JP] Japan ................................ 61-314784

[51] Int. Cl.$^5$ ............................................. A61B 5/02
[52] U.S. Cl. ..................................................... 128/633
[58] Field of Search ........................................... 128/633

[56] References Cited

U.S. PATENT DOCUMENTS

| | | | |
|---|---|---|---|
| 3,998,550 | 12/1976 | Konishi et al. | 128/633 X |
| 4,029,085 | 6/1977 | Dewitt et al. | 128/633 |
| 4,167,331 | 9/1979 | Nielsen | 128/633 X |
| 4,222,389 | 9/1980 | Rubens | 128/633 |
| 4,336,809 | 6/1982 | Clark | 128/665 |
| 4,427,889 | 1/1984 | Muller | 128/633 |
| 4,449,535 | 5/1984 | Renault | 128/665 |
| 4,463,762 | 8/1984 | Rubens | 128/633 |
| 4,513,751 | 4/1985 | Abe et al. | 128/633 |
| 4,622,974 | 11/1986 | Coleman | 128/634 |
| 4,694,833 | 9/1987 | Hamaguri | 128/633 |

FOREIGN PATENT DOCUMENTS

0129786 10/1979 Japan ................................ 128/665

OTHER PUBLICATIONS

Melville, A. W. et al. "An Improved Recording Oximeter", Electronic Engrg. vol. 32 #38 May 1960 pp. 296-300.

Nichols, R. A. et al. "Oximeter", EP 0194105, Europ. Pat. Appli., published Oct. 9, 1986.

*Primary Examiner*—Francis Jaworski
*Attorney, Agent, or Firm*—Sughrue, Mion, Zinn, Macpeak & Seas

[57] ABSTRACT

An apparatus for measuring the change in the concentration of a pigment in blood is disclosed which comprises: light quantity detecting units for continuously detecting the quantities of radiations of light having different wavelengths that have been transmitted or reflected by living tissue containing pulsating blood; first computing unit which, when the concentration or absorptivity coefficient of a light-absorbing component in the blood changes with respect to light having either one of said wavelengths, computes the quantities of radiations of transmitted or reflected light having the wavelengths when the living tissue is in a state of ischemia on the basis of the constant and pulsating components of the quantity of each radiation of light that has been detected by the light quantity detectors both before and after the change occurred; and second computing unit which continuously determines the concentration of a pigment of interest in the blood by performing calculations based on the results of computation by the first computing means and on the quantities of radiations of light detected by the light quantity detecting units.

12 Claims, 4 Drawing Sheets

APPARATUS FOR MEASURING THE CHANGE IN THE CONCENTRATION OF A PIGMENT IN BLOOD

This is a continuation-in-part of application Ser. No. 7/515,527 filed Apr. 26, 1990, and now abandoned which is a continuation of 7/138,111 filed Dec. 28, 1987 and now abandoned.

BACKGROUND OF THE INVENTION

The present invention relates to an apparatus for continuously measuring the change in the concentration of a pigment in blood in a living tissue.

A technique known as pulse oximetry is capable of measuring the concentration of a pigment in the arterial blood in a living tissue in a noninvasive and continuous manner. However, the number of measurements that can be attained by this technique per heart beat is usually one, and no more than a few at maximum. This is because in order to attain one value of measurement by pulse oximetry, it is necessary to detect the quantity of light that has been transmitted through a pulsating blood at least two points of time, which must be kept apart by a certain amount in order to ensure a correct value of measurement.

The technique of pulse oximetry has the disadvantage that when the oxygen saturation of blood changes very rapidly or in such a case where the cardiac output is to be calculated from a pigment dilution curve constructed by injecting a pigment into a blood vessel, it is impossible to measure the change in the concentration of the pigment in a fully continuous manner regardless of the cycle of heart beats.

The present invention has been accomplished in order to eliminate this defect of the prior art technique. An object, therefore, of the present invention is to provide an apparatus capable of measuring the concentration of a pigment in blood in a noninvasive and fully continuous manner.

SUMMARY OF THE INVENTION

The apparatus of the present invention comprises: light quantity detecting means for continuously detecting the quantities of radiations of light having different wavelengths that have been transmitted or reflected by a living tissue containing pulsating blood; first computing means which, when the concentration or absorptivity coefficient of a light-absorbing component in said blood changes with respect to light having either one of said wavelengths, computes the quantities of radiations of transmitted or reflected light having said wavelengths when said living tissue is supposed in a state of ischemia on the basis of the constant and pulsating components of the quantity of each radiation of light that has been detected by said light quantity detecting means both before and after said change occurred; and second computing means which continuously determines the concentration of a pigment of interest in said blood by performing calculations based on the results of computation by said first computing means and on the quantities of radiations of light detected by said light quantity detecting means.

The change in the concentration of a light-absorbing component may also be expressed as the change in the absorptivity of blood, so in the following description of the present invention discussion is made by referring to the change in absorptivity coefficient. The light quantity detecting means used in the apparatus of the present invention detects the quantity of light transmitted or reflected by a living tissue. The term "radiation of light reflected by a living tissue" means the light incident upon a living tissue that is refracted internally to go outside the tissue. The following description is directed solely to transmitted light but it should be noted that the same explanation holds good for reflected light.

DETAILED DESCRIPTION OF THE INVENTION

The apparatus of the present invention is operated in the following manner. The operator first causes a change in the absorptivity coefficient of blood with respect to a radiation of light having one wavelength. The first computing means determines the constant and pulsating components of the quantity of each of the radiations of transmitted light having different wavelengths on the basis of their quantities detected by said light quantity detecting means both before and after said change occurred, and computes from the determined values the ischemic level, in other words, the estimated quantity of each radiation of transmitted light when a living tissue being analyzed is in a state of ischemia. The second computing means continuously computes the concentration of a pigment of interest in blood on the basis of the ischemic levels computed by the first computing means and the quantities of radiations of light detected by the light quantity detecting means.

The operating principle of an apparatus according to one embodiment of the present invention is hereunder described.

Figure 2:
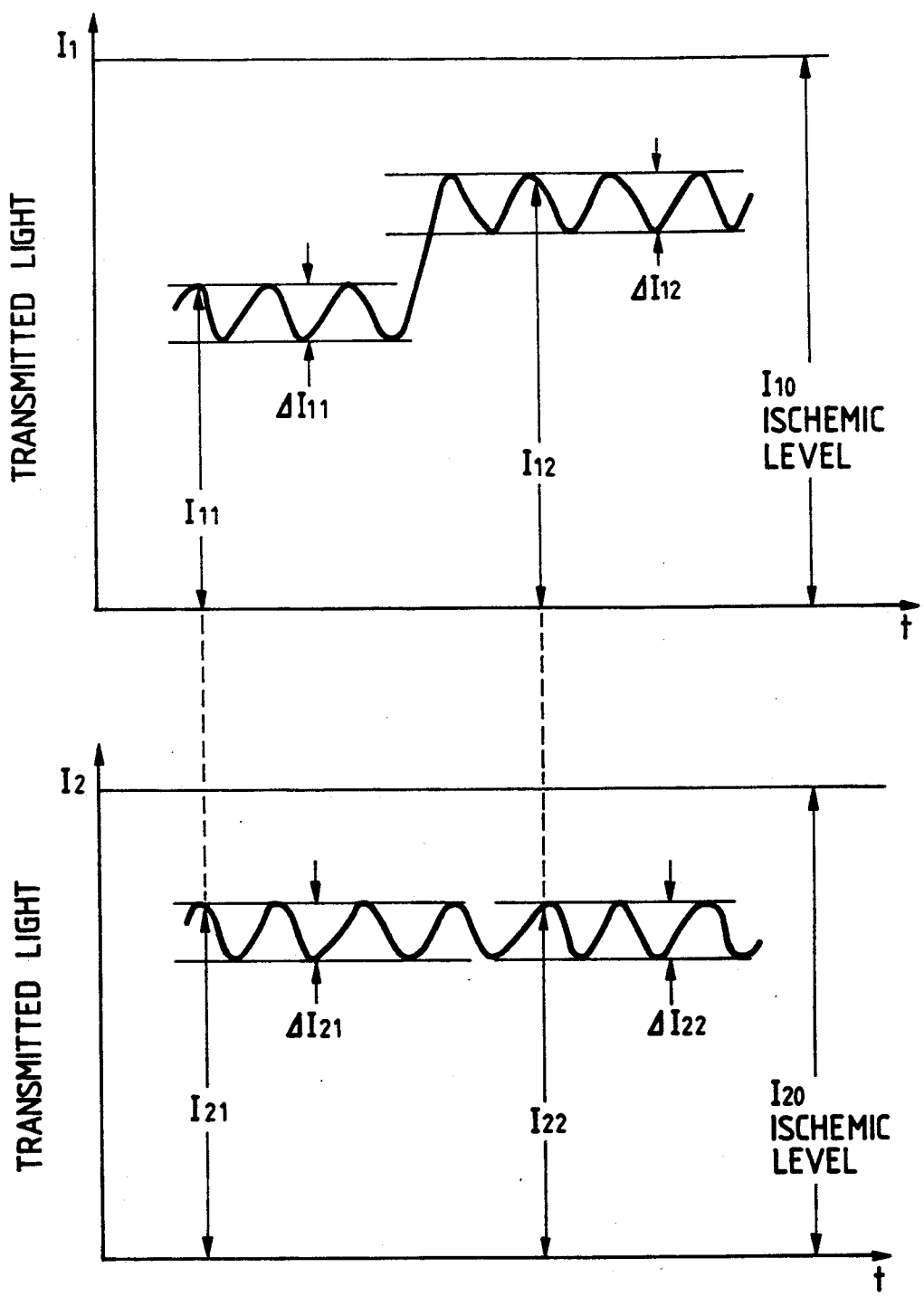
FIGS. 2 and 3 are diagrams illustrating the operating principle of the apparatus shown in FIG. 1.

Radiations of light having two different wavelengths, $\lambda_1$ and $\lambda_2$, are transmitted through a living tissue and the absorptivity coefficient of blood with respect to one wavelength, $\lambda_1$, is changed at a certain point of time by, for example, injecting a pigment into a blood vessel. FIG. 2 shows the resulting changes in the quantities of two radiations of transmitted light, $I_1$ and $I_2$. as shown, the values of $I_1$ and $I_2$ are subject to change in response to blood pulsations. In FIG. 2, the constant and pulsating components of transmitted light having a wavelength of $\lambda_1$ (or $\lambda_2$) before the absorptivity coefficient was changed are expressed by $I_{11}$ (or $I_{21}$) and $\Delta I_{11}$ (or $\Delta I_{21}$), respectively, and the constant and pulsating components of transmitted light having an wavelength of $\lambda_1$ (or $\lambda_2$) after the absorptivity coefficient was changed are expressed by $I_{12}$ (or $I_{22}$) and $\Delta I_{12}$ (or $\Delta I_{22}$), respectively. Suppose here that the absorptivity coefficient of blood with respect to light having the wavelength $\lambda_1$ is $E_{11}$ before it was changed, and $E_{12}$ after it was changed. On the other hand, the absorptivity coefficient of blood with respect to light having the wavelength $\lambda_2$ assumes a constant value of $E_2$.

If the quantities of radiations of light having wavelengths $\lambda_2$ and $\lambda_2$ that have been transmitted through a living tissue in a state of ischemia are written as $I_{10}$ and $I_{20}$, respectively, then the following equations will hold good according to the general formula for determining the absorbance of light transmitted through a living tissue:

$$\log\{I_{10}/(I_{11}-\Delta I_{11})\} = E_{11}C(D_1+\Delta D_1) \quad (1)$$

$$\log\{I_{10}/(T_{12}-\Delta I_{12})\} = E_{12}C(D_2+\Delta D_2) \quad (2)$$

$$\log\{I_{20}/(I_{21}-\Delta I_{21})\} = E_2C(D_1+\Delta D_1) \quad (3)$$

$$\log\{I_{20}/(I_{22}-\Delta I_{22})\} = E_2C(D_2+\Delta D_2) \quad (4)$$

where C signifies the concentration of pigment contained in blood; $D_1$ and $\Delta D_1$ denote the constant and pulsating components, respectively, of the thickness of a blood layer before the absorptivity coefficient was changed; and $D_2$ and $\Delta D_2$ denote the constant and pulsating components, respectively, of the thickness of blood layer after the absorptivity coefficient was changed.

We define as $\Delta \log I = \log I - \log(I - \Delta I)$, then equation (1) can be rewritten as follows:

$$\log I_{10} - \log I_{11} + \Delta \log I_{11} - E_{11}CD_1 + E_{11}C\Delta D_1.$$

Equations (2) to (4) can be rewritten in like manner. When the pulsating and constant components are separately extracted from each of the rewritten equations, the following relations are established:

Pulsating components:

$$\Delta \log I_{11} = E_{11}C\Delta C_1 \quad (5)$$

$$\Delta \log I_{12} = E_{12}C\Delta D_2 \quad (6)$$

$$\Delta \log I_{21} = E_2 C \Delta D_1 \quad (7)$$

$$\Delta \log I_{22} = E_2 C \Delta D_2 \quad (8)$$

Constant components:

$$\log(I_{10}/I_{11}) = E_{11}C\Delta D_1 \quad (9)$$

$$\log(I_{10}/I_{12}) = E_{21}C\Delta D_2 \quad (10)$$

$$\log(I_{10}/I_{12}) = E_{21}C\Delta D_2 \quad (11)$$

$$\log(I_{20}/I_{22}) = E_2 C \Delta D_2 \quad (12)$$

Divide equation (5) by equation (7) and write the quotient as $\Phi_1$. In like manner, divide equation (6) by equation (8) and write the quotient as $\Phi_2$. The results are as follows:

$$\Phi_1 = E_{11}/E_2 = \Delta \log I_{11}/\Delta \log I_{21} \quad (13)$$

$$\Phi_2 = E_{12}/E_2 = \Delta \log I_{12}/\Delta \log I_{22} \quad (14).$$

By measuring the values of $\Delta \log I_{11}$, $\Delta \log I_{21}$, $\Delta \log I_{12}$ and $\Delta \log I_{22}$, $\Phi_1$ and $\Phi_2$ can be determined from equations (13) and (14)

From equations (9) and (11), the following relation is obtained:

$$\log(I_{10}/I_{11})/\log(I_{20}/I_{21}) = E_{11}/E_{12}.$$

Since $E_{11}/E_2 = \Phi_1$ (see equation (13)), $$\Phi_1 = \log(I_{10}/I_{11})/\log(I_{20}/I_{21}) \quad (15)$$

In like manner, the following equation is derived from equations (10) and (12):

$$\Phi_2 = \log(I_{10}/I_{12})/\log(I_{20}/I_{22}) \quad (16)$$

From equation (15) and (16), $$\log I_{10} = \{\Phi_1 \Phi_2 \log(I_{22}/I_{21}) - \Phi_1 \log I_{12} + \Phi_2 \log I_{11}\}/(\Phi_2 - \Phi_1) \quad (17)$$

$$\log I_{20} = \{\Phi_2 \log I_{22} - \Phi_1 \log I_{21} + \log(I_{11}/I_{12})\}/(\Phi_2 - \Phi_1) \quad (18)$$

By determining the values of $\Phi_1$, $\Phi_2$, $I_{11}$, $I_{12}$, $I_{21}$ and $I_{22}$, two ischemic levels $I_{10}$ and $I_{20}$ can be calculated from equations (17) and (18), respectively.

Using the so determined ischemic levels $I_{10}$ and $I_{20}$, a pigment dilution curve is constructed in the following manner.

First suppose that a pigment to be injected into a blood vessel has an absorptivity coefficient of $E_g$ with respect to light having a wavelength of $\lambda_1$, and a value of zero (no light absorption) with respect to light having a wavelength of $\lambda_2$. Also suppose that this pigment is present in blood at a concentration of $C_g$. The hemoglobin in blood is supposed to have an absorptivity coefficient of $E_{b1}$ with respect to light having a wavelength of $\lambda_1$, and $E_{b2}$ with respect to light having a wavelength of $\lambda_2$.

Figure 3:
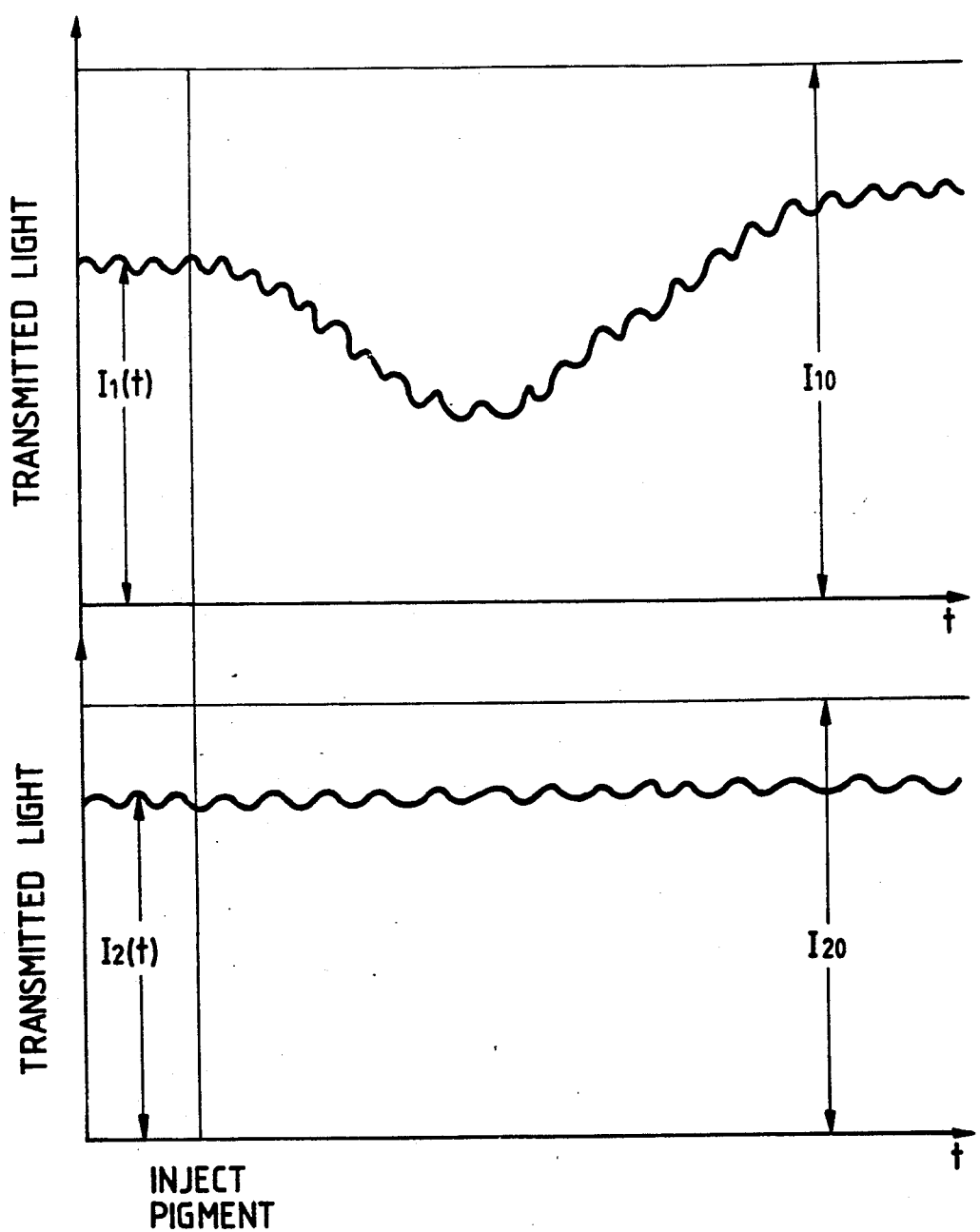

The quantity of light having the wavelength $\lambda_1$ that has been transmitted through a living tissue is a function of time and can be written as $I_1(t)$. In like manner, the quantity of light having the wavelength $\lambda_2$ that has been transmitted through the living tissue is written as $I_2(t)$ D is a function time and hence, can be expressed as $D(t)$. FIG. 3 shows the changes with time of $I_1(t)$ and $I_2(t)$ as measured before and after the injection of a pigment. Using the ischemic levels, $I_{10}$ and $I_{20}$, the absorbance of light that has been transmitted through a blood layer having a thickness of D can be expressed as follows:

$$\log\{I_{10}/I_1(t)\} - E_{b1}C_b D(t) + E_g C_g D(t) \quad (19)$$

$$\log\{I_{20}/I_2(t)\} - E_{b2}C_b D(t) \quad (20).$$

Divide equation (19) by equation (20) and write the quotient as follows:

$$\Psi(t) = \log\{I_{10}/I_1(t)\}/\log\{I_{20}/I_2(t)\} \quad (21)$$

Then, the following relation is obtained:

$$\Psi(t) = (E_{b1}C_b + E_g C_g)/E_{b2}C_b \quad (22).$$

Equation (22) can be rewritten as:

$$C_g - \{\Psi(t) - (E_{b1}/E_{b2})\} \cdot (E_{b2}/E_g) \cdot C_b \quad (23).$$

Since $E_{b1}/E_{b2}$ is equal to $E_{11}/E_2$ (both values indicate the ratio of the absorptivity coefficient of hemoglobin in blood for light having a wavelength of $\lambda_1$ to that of hemoglobin in blood for light having a wavelength of $\lambda_2$), $$E_{b1}/E_{b2} = \Delta \log I_{11}/\Delta \log I_{21} = \Phi_1 \quad (24).$$

Therefore, equation (23) can be rewritten either as:

$$C_g 32 \{\Psi(t) - \Phi_1\} \cdot (E_{b2}/E_g) \cdot C_b \quad (25),$$

or as:

$$G_g = \{\log(I_{10}/I_1(t)/\log(I_{20}/I_2(t)) - \Phi_1\}(E_{b2}/E_g)C_b \quad (26).$$

In these equations, $E_{b2}/E_g$ is known, $C_b$ can be determined by actual measurement on collected blood, and $\Phi_1$, $I_{10}$ and $I_{20}$ can be computed in the manner already described. Therefore, the time-dependent change in the concentration of a pigment of interest in blood can be determined over an adequately continuous period of time.

Figure 1:
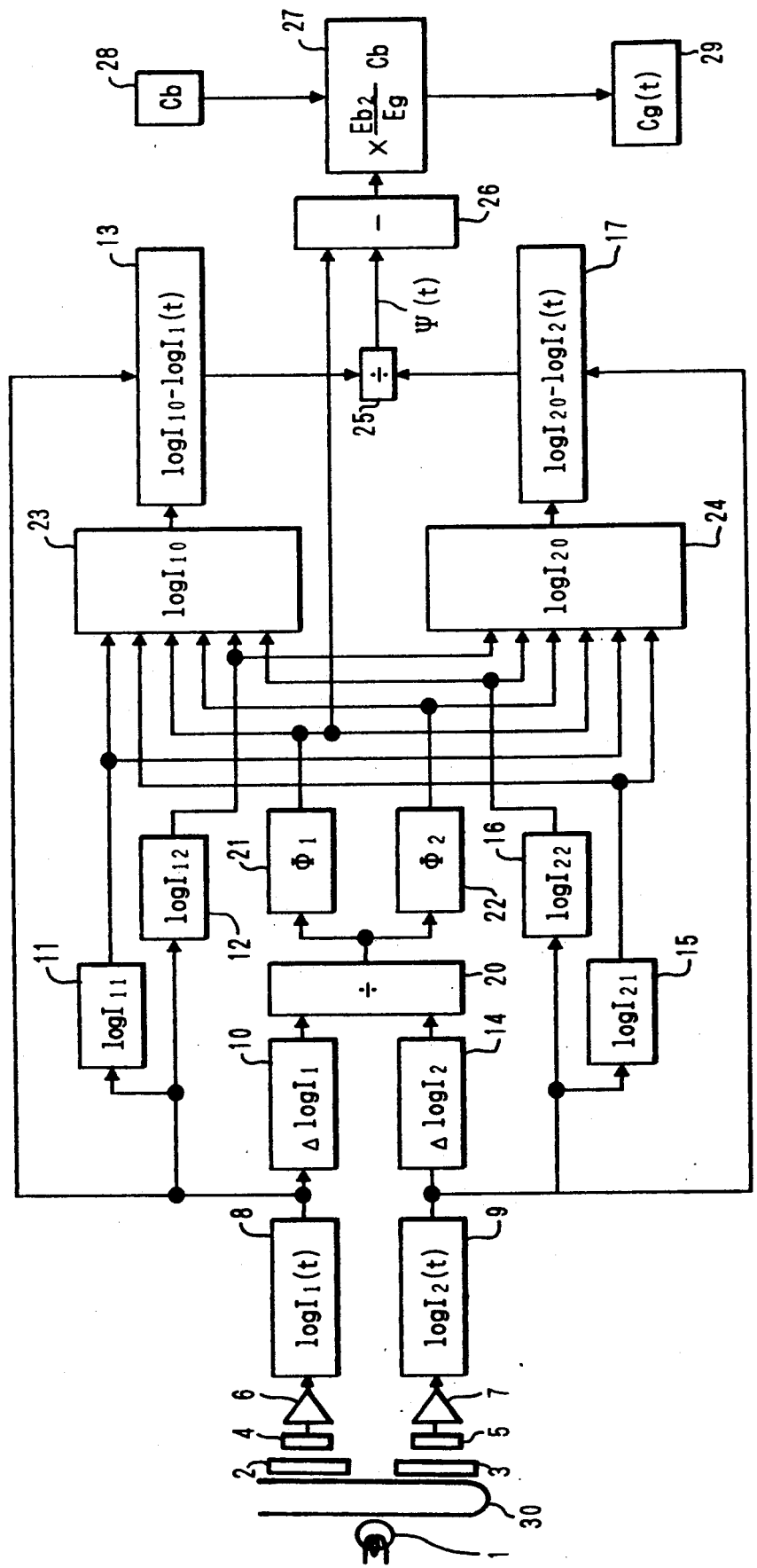
FIG. 1 is a schematic block diagram of an apparatus according to one embodiment of the present invention.

An example of the apparatus that is designed to operate by the principle outlined above is described hereinafter. FIG. 1 is a schematic block diagram of the apparatus. In the figure, a light source is denoted by the numeral 1. Light issuing from this light source 1 is transmitted to light-receiving elements 4 and 5 through optical filters 2 and 3, respectively. The filter 2 transmits light having a wavelength of $\lambda_1$, and the filter 3 transmits light having a wavelength of $\lambda_2$. Amplifier circuits 6 and 7 amplify the output signals from light-receiving elements 4 and 5, respectively. The optical filters 2 and 3, light-receiving elements 4 and 5, and amplifier circuits 6 and 7 combine to make light quantity detecting means.

The output signals from amplifier circuit 6 and 7 are supplied to logarithm computing circuits 8 and 9, respectively. Each of the circuits 8 and 9 convert the value of supplied signal to a logarithmic value and outputs a signal indicative of that logarithmic value. The output signal from the circuit 8 is supplied to each of a pulsating component extracting circuit 10, constant component extracting circuits 11 and 12, and a subtracter circuit 13. The output signal from the circuit 9 is supplied to each of the pulsating component extracting circuit 14, constant components extracting circuits 15 and 16, and a subtracter circuit 17. The circuits 10 and 14 extract the pulsating components of the output signals from logarithm computing circuits 8 and 9 and output the extracted pulsating components to a divider circuit 20. The divider circuit 20 divides the value of the output signal from the pulsating component extracting circuit 10 by the value of the output signal from the pulsating component extracting circuit 14, and supplies an appropriate signal to each of a $\Phi_1$ memory circuit 21 and a $\Phi_2$ memory circuit 22. The output signals from constant component extracting circuits 11 and 12 and from $\Phi_1$ memory circuit 21, and the output signals from constant component extracting circuits 15 and 16 and from $\Phi_2$ memory circuit 22 are supplied to an ischemic level computing circuits 23 and 24. All of the circuits mentioned above are controlled in such a way that they are operated with a timing, the values of which are predetermined by a control circuit (not shown). The constant component extracting circuits 11 and 12 extract, in response to a timing signal from said control circuit, the constant components of the output signal from the logarithm computing circuit 8 and store the extracted components. The constant component extracting circuits 15 and 16 extract, in response to a timing signal from said control circuit, the constant components of the output signal from the logarithm computing circuit 9 and store the extracted components. Each of the $\Phi_1$ and $\Phi_2$ memory circuits 21 and 22 stores the value of the output signal from the divider circuit 20 in response to a timing signal from said control circuit. The ischemic level computing circuit 23 (or 24) performs necessary calculations on the basis of the values stored in the constant component extracting circuits 11, 12, 15 and 16 and in the $\Phi_1$ memory circuit 21 and $\Phi_2$, memory circuit 22, determines the logarithm of the ischemic level for light having a wavelength of $\lambda_1$ (or $\lambda_2$), and stores the determined logarithmic value. the logarithm computing circuit 8 and 9, the pulsating component extracting circuits 10 and 14, the divider circuit 20, the constant component extracting circuits 11, 12, 15 and 16, the $\Phi_1$ memory circuit 21, the $\Phi_2$ memory circuit 22, and the ischemic level computing circuits 23 and 24 combine to make first computing means.

Shown by 13 and 17 in FIG. 1 are subtracter circuits. The subtracter 13 (or 17) determines the difference between the value of output signal from the ischemic level computing circuits 23 (or 24) and the value of output signal from the logarithm computing circuits 8 (or 9) and outputs the difference to a divider circuits 25. The divider circuit 25 divides the value of output signal from the subtracter circuits 13 by the value of output signal from the subtracter 17, and outputs the results to a subtracter circuit 26. The subtracter circuit 26 determines the difference between the value of output signal from the divider circuit 25 and the value of output signal from the $\Phi_1$ memory circuit 21 and outputs the results to a multiplier circuit 27. The multiplier circuit 27 multiplies the value of output signal from the subtracter circuit 26 by a value associated with the value stored in a memory circuit 28, and outputs the product to a recording unit 29. The memory circuit 28 stores an externally set value of the hemoglobin concentration in blood. The subtracter circuits 13 and 17, the divider circuit 25, the subtracter circuit 26, the multiplier circuit 27, and the memory circuit 28 combine to make second computing means.

The apparatus having the construction described above will be operated in the following manner.

In the first step, the operator prepares a part of the living tissue to be analyzed and sets the part of the living sample 30 between light source 1 and each of the optical filters 2 and 3. As a result, the logarithm computing circuits 8 and 9 output signals that represent $\log I_1(t)$ and $\log I_2(t)$, respectively, which are the logarithms of $I_1(t)$ and $I_2(t)$. The quantities of radiations of light having wavelengths of $\lambda_1$ and $\lambda_2$ that have been transmitted through the part of the living tissue 30 correspond to the values $I_1(t)$ and $I_2(t)$, respectively. The operator, after recognition of a steady-state situation indicates to the device the time to calculate and store $\log I_{11}$, $\log I_{21}$ and $\Phi_1$, with a signal generated, for example, by pushing a foot switch (not shown). Receiving this generated signal, the aforementioned control circuit (not shown) outputs a predetermined timing signal to each of the constant component extracting circuits 11 and 15 and the $\Phi_1$ memory circuit 21. In response to this timing signal, the circuit 11 (or 15) extracts the constant component per heart beat of the signal value supplied from the logarithm computing circuit 8 (or 9) over a given duration of time, calculates the average of the extracted constant components, and stores the calculated average. The value stored in the constant component circuit 11 is $\log I_{11}$, shown in FIG. 2, which is the logarithm of $I_{11}$, or logarithm of the quantity or transmitted light having the wavelength $\lambda_1$ and the value stored in the constant component circuit 15 is $\log I_{21}$, also shown in FIG. 2, which is the logarithm of $I_{21}$, or the logarithm of the quantity of transmitted light having the wavelength $\lambda_2$. The $\Phi_1$ memory circuit 21 also determines the average of signal values supplied per heart beat from the divider circuit 20 over the same duration of time, and stores this average. The value stored in the $\Phi_1$ memory circuit 21 is $\Phi_1$ which is expressed by equation (13).

In the next step, the operator causes a change in the absorptivity coefficient of blood in part of the living tissue 30 with respect to light having a wavelength of $\lambda_1$. This may be done by changing the oxygen saturation of blood or by injecting a pigment into a blood vessel. After a change has occurred in the absorptivity coefficient of blood, the operator indicates to the device the time to calculate the and store log $I_{12}$, log $I_{22}$ and $\Phi_2$ with a signal generated, for example, by pushing a button (not shown). Receiving this generated signal, the control circuit (not shown) supplies a predetermined timing signal to each of the constant component extracting circuits 12 and 16 and the $\Phi_2$ memory circuit 22. In response to this timing signal, the constant component extracting circuit 12 (or 16) extracts the constant component per heart beat of the signal value supplied from the logarithm computing circuit 8 (or 9) over a given duration of time, calculates the average of these constant components, and stores the calculated average. The value stored in the constant component extracting circuit 12 is log$I_{12}$, shown in FIG. 2, which is the logarithm of $I_{12}$, or the logarithm of quantity transmitted light having the wavelength $\lambda_1$ and the logarithm of value stored in the constant component extracting circuit 16 is log$I_{22}$, also shown in FIG. 2, which is the logarithm of $I_{22}$, or the logarithm of the quantity of transmitted light having the wavelength $\lambda_2$. The $\Phi_2$ memory circuit 22 also determines the average of signal values supplied per heart beat from the divider circuit 20 over a second period of time having the same predetermined length of duration, and stores this average. The value stored in the $\Phi_2$ memory circuit 22 is $\Phi_2$ expressed by equation (14).

The control circuit (not shown) then supplies a predetermined timing signal to each of the ischemic level computing circuits 23 and 24. In response to this signal, the ischemic level computing circuit 23 (or 24) calculates Log $I_{10}$ (or Log $I_{20}$) which is the logarithm of the ischemic level $I_{10}$ (or $I_{20}$) in accordance with equation (17) (or (18)).

In a subsequent step, the operator injects into the blood vessel 30 a pigment whose concentration is to be measured. The operator at the time of injection indicates to the device the time to start calculation of the concentration of pigment in the blood by a signal generated, for example, by pushing a foot switch. Receiving this generated signal, the control circuit supplies a timing signal to the subtracter circuits 13 and 17, the divider circuit 25, the subtracter circuit 26 and the multiplier circuit 27. The subtracter circuit 13 (or 17) calculates the difference between log$I_{10}$ (or log$I_{20}$) stored in the ischemic level computing circuit 23 (or 24) and log$I_1(t)$ (or log$I_2(t)$) supplied from the logarithm computing circuit 8 (or 9), and outputs the difference to the divider circuits 25. Accordingly, the divider circuits 25 outputs $\Psi(t)$ expressed by equation (21). Then, the subtracter circuit 26 calculates the difference between $\Psi(t)$ and the value of $\Phi_1$ stored in $\Phi_1$ memory circuit 21, and outputs the difference to the multiplier circuit 27. The multiplier circuits 27 holds a preliminarily loaded value of $(E_{b2}/E_g) \cdot C_b$, in which the component $C_b$ is supplied from the memory circuit 28 and, in the case under discussion, denotes the concentration of hemoglobin in the blood preliminarily collected from the patient. The multiplier circuit 27 multiplies the value of $(\Psi(t) - \Phi_1)$ from the subtracter circuit 26 by $(E_{b2}/E_g) \cdot C_b$, and outputs the product to the recording unit 29. In this way, the multiplier circuit 27 determines $C_g(t)$ by performing calculations in accordance with equation (25) or (26). The values of $C_g(t)$ are recorded with unit 29 in a fully continuous manner.

In the embodiment under discussion, $\Phi_2$, log$I_{12}$ and log$I_{22}$ to be used in calculating ischemic levels are determined by merely obtaining a single value of each parameter per heart beat and averaging the individual values, as in the case of determining fairly stable $\Phi_1$, log$I_{11}$ and log$I_{21}$ (i.e., the values before pigment injection). However, this method is not capable of providing the correct values since $\Phi_2$, log$I_{12}$ and log$I_{22}$, which are the values obtained either after pigment injection or after the change in the oxygen saturation of blood, have experienced marked changes. In order to overcome this defect, $\Phi_2$, log$I_{12}$ and log$I_{22}$ are calculated by first obtaining a plurality of values for each parameter from the data for one heart beat, then averaging these values. In the next place, the so determined values for each heart beat are stored as they are. In determining ischemic levels, the values of $\Phi_2$, log$I_{11}$ and log$I_{21}$ for each heart beat are combined with those of $\Phi_1$, log$I_{11}$ and log$I_{21}$ for each heart beat (the value of each parameter in the second group is stable and may be determined by averaging the values for a plurality of heart beats as described above) so as to compute log$I_{10}$ and log$I_{20}$ for each heart beat. After computing these values of log$I_{10}$ and log$I_{20}$, these within the range where the pigment concentration is sufficiently high to be fairly stable are selected and averaged. The so obtained values of log$I_{10}$ and log$I_{20}$ are highly reliable and permit correct measurement of the change in pigment concentration.

In working with the apparatus shown in FIG. 1, the operator is required to perform a prescribed sequence of operations each for the case of determining ischemic levels and for the case of constructing a pigment dilution curve $C_g(t)$ on the basis of the so determined ischemic levels. If desired, the operator may inject a pigment at a certain point of time, record all the values of log$I_1(t)$ and log$I_2(t)$ in a continuous manner over a duration of time including that point of time, determine ischemic levels by subsequently analyzing the recorded data, and construct a pigment dilution curve on the basis of the so determined ischemic levels. This method has the advantage that the operator needs to inject a pigment only once into the sample of living tissue to be analyzed.

Figure 4:
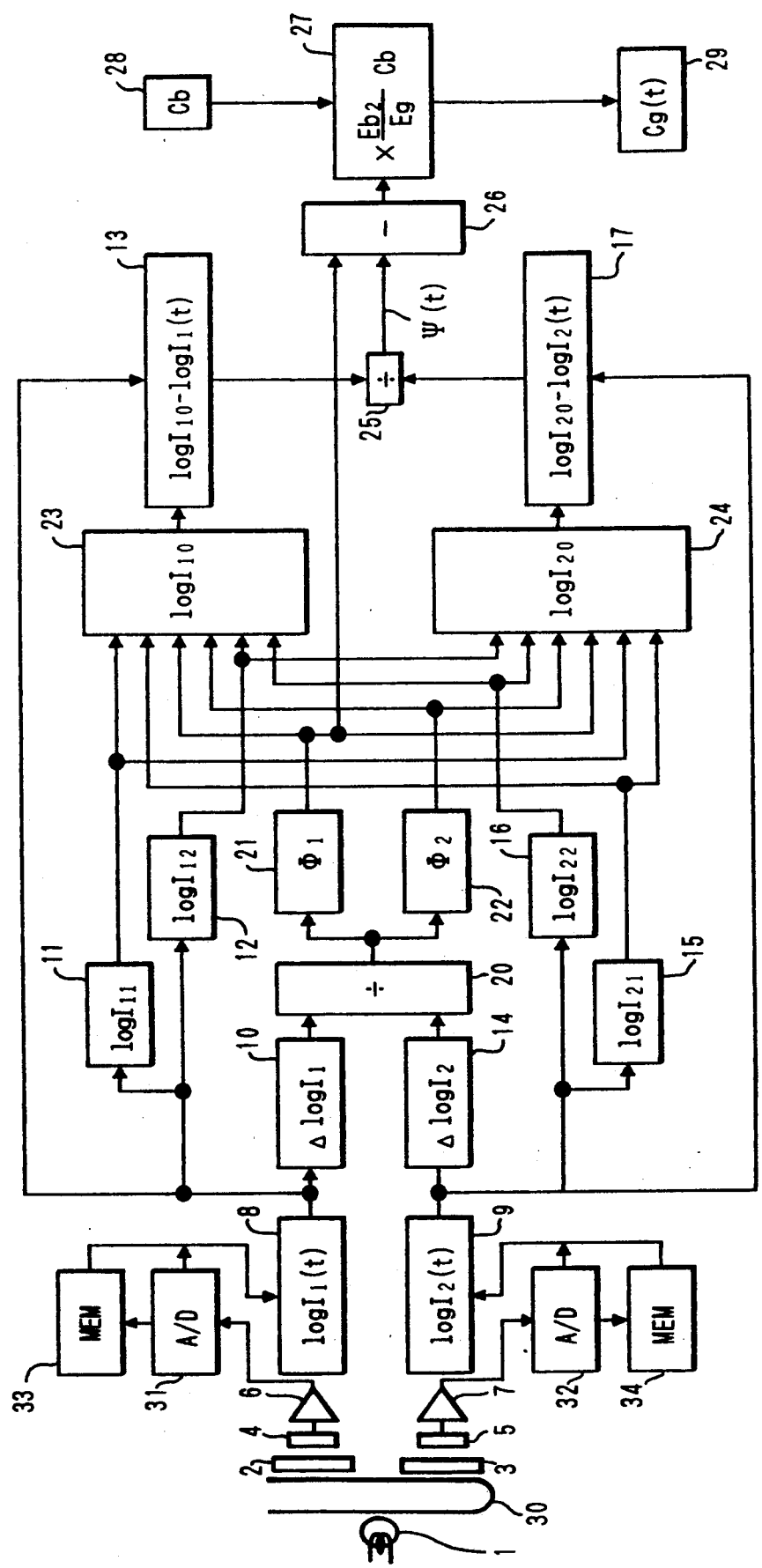
FIG. 4 is a block diagram showing a digital implementation of the apparatus of FIG. 1.

The apparatus shown in FIG. 1 is composed of analog circuitry. However, more rapid and precise measurements can be attained by performing A/D conversion on the signals produced from the light quantity detecting means, then performing subsequent processing with an electronic computer. An embodiment of the above-mentioned digital implementation is shown in FIG. 4. More specifically, this implementation includes an A/D converter 31 and an associated memory means 33, an A/D converter 32 and an associated memory means 34. The A/D converter 31 and memory 33 are connected between boxes 6 and 8, and converter 32 and memory means 34 are connected between boxes 7 and 9. The boxes 10-29 of FIG. 1 are also shown in the embodiment of FIG. 4. However, in the embodiment of FIG. 4 these elements constitute a digital processor. The operation of the embodiment of FIG. 4 is similar to the operation of FIG. 1 as discussed above.

Although a single light source and two light receiving elements are used in the foregoing embodiment, it is apparent that the invention is not limited thereto and thereby. For example, it is possible to use a single light receiving element for two alternatively lighting light sources in a time-divisional manner.

As described on the foregoing pages, the apparatus of the present invention is capable of measuring the change in the concentration of a pigment in blood in a fairly noninvasive and fully continuous manner.

What is claimed is:

1. An apparatus for measuring a change in the concentration of a pigment injected into a blood vessel, an absorptivity coefficient of the blood being changed with respect to a first wavelength of light, the apparatus comprising:
    light quantity detecting means for continuously detecting quantities of radiation of light which have been transmitted/reflected by a living tissue containing pulsating blood, one of the detected radiations of light transmitted/reflected by the living tissue having the first wavelength of light;
    first computing means for converting outputs from said light quantity detecting means to logarithmic values and for determining constant and pulsating components of the logarithmic values of each wavelength both before and after the change in the absorptivity coefficient of the blood, and for computing estimated transmitted/reflected light level of a supposed ischemic tissue, from the determined constant and pulsating components; and
    second computing means for continuously computing the concentration of pigment injected into the blood vessel according to the estimated transmitted/reflected light level of the supposed ischemic tissue computed by said first computing means and according to the quantities of radiation of light detected by said light quantity detecting means.

2. The apparatus according to claim 1, further comprising a light source for supplying light having different wavelengths, and wherein said light quantity detecting means comprises:
    light filter means for receiving light from said source and for transmitting a plurality of light beams, each of the plurality of transmitted light beams having a different wavelength, and one of the plurality of light beams having the first wavelength of light; and
    light receiving means for receiving the different wavelengths of light transmitted from said light filter means.

3. The apparatus according to claim 1, wherein said first computing means comprises:
    logarithmic circuit means for receiving the output of said light quantity detecting means and for converting the output from said light quantity detecting means to a logarithmic value;
    constant component extracting means for extracting a value from the converted-logarithmic value which represents a pulsating component; and
    ischemic level computing means for detecting the supposed ischemic level of the blood vessel according to the extracted constant and pulsating components.

4. The apparatus according to claim 1, wherein said second computing means includes calculation means for calculating a time-dependent change in the concentration of the injected pigment.

5. The apparatus according to claim 4, wherein said second computing means further includes recording means for recording the output of said calculation means.

6. The apparatus according to claim 1, further comprising an analog-to-digital converter for converting the outputs of said light quantity detecting means to digital signals, memory means for storing an output of said analog-to-digital converter, means for supplying data of said memory means to said first computing means so said first computing means can compute the estimated light level of the supposed ischemic tissue, and for supplying data of said memory means to said second computing means so said second computing means can compute the concentration of pigment in the blood continuously using the estimated light level of the supposed ischemic tissue.

7. The apparatus according to claim 6, wherein the first and second computing means are each digital computing means.

8. The apparatus according to claim 6, wherein said first and second computing means are implemented in an electronic computer.

9. The apparatus according to claim 1, wherein said light quantity detecting means includes a first and a second photoelectric device, said first photoelectric device only detecting the first wavelength of radiated light, and said second photoelectric device only detecting a second wavelength of light which is different than the first wavelength of light, and wherein said first computing means determines the constant and pulsating components of the output of each of said first and second photoelectric devices.

10. The apparatus according to claim 1, wherein the injected pigment has a different absorptivity coefficient than a light-absorbing component in the blood.

11. The apparatus according to claim 1, wherein the absorptivity coefficient of the blood is changed with respect to the first wavelength by injecting a dye into the blood.

12. An apparatus for measuring a change in the oxygen saturation of blood, an absorptivity coefficient of the blood being changed with respect to a first wavelength of light, the apparatus comprising:
    light quantity detecting means for continuously detecting quantities of radiation of light which have been transmitted/reflected by a living tissue containing pulsating blood, one of the detected radiations of light transmitted/reflected by the living tissue having the first wavelength of light;
    first computing means for converting outputs from said light quantity detecting means to logarithmic values and for determining constant and pulsating components of the logarithmic values of each wavelength both before and after the change in the absorptivity coefficient of the blood, and for computing estimated transmitted/reflected light level of a supposed ischemic tissue, from the determined constant and pulsating components; and
    second computing means for continuously computing the oxygen concentration of the blood vessel according to the estimated transmitted/reflected light level of the supposed ischemic tissue computed by said first computing means and according to the quantities of radiation of light detected by said light quantity detecting means.

* * * * *